US008865091B2

(12) United States Patent
Dufresne et al.

(10) Patent No.: US 8,865,091 B2
(45) Date of Patent: *Oct. 21, 2014

(54) MULTILAYER PROCESSING DEVICES AND METHODS (75) Inventors: Joel R. Dufresne, St. Paul, MN (US); Bryan C. Feisel, Hudson, WI (US); Theresa J. Gerten, Eagan, MN (US); Brent R. Hansen, New Richmond, WI (US); David D. Nguyen, Savage, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 24 days.

This patent is subject to a terminal disclaimer.

(21) Appl. No.: 12/749,763

(22) Filed: Mar. 30, 2010

(65) Prior Publication Data
US 2010/0183479 A1 Jul. 22, 2010

Related U.S. Application Data (62) Division of application No. 10/682,597, filed on Oct. 9, 2003, now Pat. No. 7,718,133.

(51) Int. Cl.
*G01N 3/00* (2006.01)
*B01L 3/00* (2006.01)
*G01N 21/03* (2006.01)

(52) U.S. Cl.
CPC ....... *B01L 3/502715* (2013.01); *G01N 21/0303* (2013.01); *Y10S 436/809* (2013.01); *B01L 3/502707* (2013.01); *B01L 2300/0864* (2013.01); *B01L 2300/0816* (2013.01); *B01L 2300/168* (2013.01); *B01L 2200/12* (2013.01); *B01L 2300/0812* (2013.01); *B01L 2300/0887* (2013.01)
USPC ........... 422/503; 422/403; 422/430; 422/502; 422/551; 422/552; 536/164; 536/809; 156/44; 436/809

(58) Field of Classification Search
CPC . G01N 21/0303; B01L 3/00; B01L 3/502707; B01L 2300/168; B01L 2200/12; B01L 2300/0812; B01L 2300/0816; B01L 2300/0864; B01L 2300/0887; B01L 3/502715
USPC .......... 436/164, 809; 422/403, 430, 502, 503, 422/551, 552; 156/44
See application file for complete search history.

(56) References Cited

U.S. PATENT DOCUMENTS 3,856,470 A 12/1974 Cullis et al.
3,938,958 A 2/1976 Lanier et al.
(Continued)

FOREIGN PATENT DOCUMENTS

EP 0 571 661 12/1993
EP 0 402 994 B1 11/1994
(Continued)

OTHER PUBLICATIONS

*Handbook of Pressure Sensitive Adhesive Technology*, Donatas Sata (Ed.) 2nd Edition, Title page, p. 172 and FIG. 8-16 on p. 173, Van Nostrand Reinhold, New York, NY, 1989 (2 pgs).
(Continued)

*Primary Examiner* — Lyle Alexander (57) ABSTRACT

Sample processing devices that include transmissive layers and control layers to reduce or eliminate cross-talk between process chambers in the processing device are disclosed. The transmissive layers may transmit significant portions of signal light and/or interrogation light while the control layers block significant portions of signal light and/or interrogation light. Methods of manufacturing processing devices that include transmissive layers and control layers are also disclosed. The methods may involve continuous forming processes including co-extrusion of materials to form the transmissive layer and control layer in a processing device, followed by formation of the process chambers in the control layer. Alternatively, the methods may involve extrusion of materials for the control layer, followed by formation of process chambers in the control layer.

5 Claims, 4 Drawing Sheets

(56) References Cited

U.S. PATENT DOCUMENTS

| | | | |
|---|---|---|---|
| 4,390,499 A | 6/1983 | Curtis et al. |
| 4,632,908 A | 12/1986 | Schultz |
| 4,673,657 A | 6/1987 | Christian |
| 4,806,316 A | 2/1989 | Johnson et al. |
| 5,154,888 A | 10/1992 | Zander et al. |
| 5,219,526 A | 6/1993 | Long |
| 5,229,297 A | 7/1993 | Schnipelsky et al. |
| 5,248,479 A | 9/1993 | Parsons et al. |
| 5,254,479 A | 10/1993 | Chemelli |
| 5,258,163 A | 11/1993 | Krause et al. |
| 5,288,463 A | 2/1994 | Chemelli |
| 5,310,523 A | 5/1994 | Smethers et al. |
| 5,346,672 A | 9/1994 | Stapleton et al. |
| 5,422,271 A | 6/1995 | Chen et al. |
| 5,425,917 A | 6/1995 | Schmid |
| 5,457,527 A | 10/1995 | Manns et al. |
| 5,460,780 A | 10/1995 | Devaney, Jr. et al. |
| 5,587,128 A | 12/1996 | Wilding et al. |
| 5,643,738 A | 7/1997 | Zanzucchi et al. |
| 5,726,026 A | 3/1998 | Wilding et al. |
| 5,744,366 A | 4/1998 | Kricka et al. |
| 5,800,785 A | 9/1998 | Bochner |
| 5,804,141 A | 9/1998 | Chianese |
| 5,811,296 A | 9/1998 | Chemelli et al. |
| 5,833,923 A | 11/1998 | McClintock et al. |
| 5,849,208 A | 12/1998 | Hayes et al. |
| 5,863,502 A | 1/1999 | Southgate et al. |
| 5,863,708 A | 1/1999 | Zanzucchi et al. |
| 5,863,801 A | 1/1999 | Southgate et al. |
| 5,876,675 A | 3/1999 | Kennedy |
| 5,955,028 A | 9/1999 | Chow |
| 6,033,605 A | 3/2000 | Szlosek |
| 6,399,025 B1 | 6/2002 | Chow |
| 6,413,782 B1 | 7/2002 | Parce et al. |
| 6,572,830 B1 | 6/2003 | Burdon et al. |
| 6,627,159 B1 | 9/2003 | Bedingham et al. |
| 6,814,935 B2 | 11/2004 | Harms et al. |
| 7,026,168 B2 | 4/2006 | Bedingham et al. |
| 7,135,147 B2 | 11/2006 | Cox et al. |
| 7,198,759 B2 | 4/2007 | Bryning et al. |
| 7,201,881 B2 | 4/2007 | Cox et al. |
| 7,718,133 B2 * | 5/2010 | Dufresne et al. | 422/102 |
| 2002/0047003 A1 * | 4/2002 | Bedingham et al. | 219/388 |
| 2003/0183958 A1 | 10/2003 | Goff et al. |
| 2004/0121471 A1 | 6/2004 | Dufresne et al. |
| 2004/0175734 A1 | 9/2004 | Stahler et al. |
| 2005/0063877 A1 | 3/2005 | Takahashi |
| 2008/0287307 A1 | 11/2008 | Adrien et al. |

FOREIGN PATENT DOCUMENTS

| | | | |
|---|---|---|---|
| EP | 0 693 560 A2 | 1/1996 |
| JP | 8-114539 | 5/1996 |
| JP | 2000-121547 | 4/2000 |
| JP | 2001-188044 | 7/2001 |
| JP | 2002-523781 | 7/2002 |
| JP | 2002-543434 | 12/2002 |
| JP | 2003-511702 | 7/2010 |
| WO | WO 94/26414 A1 | 11/1994 |
| WO | WO 96-04547 | 2/1996 |
| WO | WO 96/15576 A1 | 5/1996 |
| WO | WO 96/34028 A1 | 10/1996 |
| WO | WO 96/34029 A1 | 10/1996 |
| WO | WO 99/44740 A1 | 9/1999 |
| WO | WO 99-46045 | 9/1999 |
| WO | WO 00/17624 | 3/2000 |
| WO | WO 00/68336 A1 | 11/2000 |
| WO | WO 01/07892 A1 | 2/2001 |
| WO | WO 01/098781 A1 | 12/2001 |
| WO | WO 02/00347 A2 | 12/2001 |
| WO | WO 02/00347 A3 | 1/2002 |
| WO | WO 02/01180 A2 | 1/2002 |
| WO | WO 02/01180 A3 | 1/2002 |
| WO | WO 02/061392 | 8/2002 |
| WO | WO 03/056517 | 7/2003 |

OTHER PUBLICATIONS

Sobieski et al., "18. Silicone Pressure Sensitive Adhesives", *Handbook of Pressure Sesitive Adhesive Technology*, Donatas Satas (Ed.) $2^{nd}$ Edition, Van Nostrand Reinhold, New York, Title page and p. 508-517 (6 pgs.).

*Test Methods for Pressure Sensitive Adhesive Tapes*, Pressure Sensitive Tape Council, 1996, Title page, Table of Contents, and p. 6 (3 pgs.).

Unger et al., "Monolithic Microfabricated Valves and Pumps by Multilayer Soft Lithography," *Science*, Apr. 7, 2000, vol. 288:113-116.

International Search Report for PCT/US2004/026546.

Annex to European Search Report for EP09176090.

\* cited by examiner

MULTILAYER PROCESSING DEVICES AND METHODS

CROSS REFERENCE TO RELATED APPLICATIONS

This application is a divisional of U.S. Ser. No. 10/682,597, filed Oct. 9, 2003 now U.S. Pat. No. 7,718,133, now allowed, the disclosure of which is incorporated by reference in its entirety herein.

BACKGROUND

A variety of devices have been designed for the simultaneous processing of chemical, biochemical, and other reactions. The devices typically include a number of wells or process chambers in which the processing is performed. Detection of various analytes or process products may be performed by detecting signal light emitted from the process chambers. The signal light may be caused by, e.g., reactions within the process chambers. In other instances, the signal light may be in response to excitation by interrogating light directed into the process chamber from an external source (e.g., a laser, etc.), where the signal light results from, e.g., chemiluminescence, etc.

Regardless of the mechanism or technique used to cause the emission of signal light from the process chambers, its detection and correlation to specific process chambers may be required. If, for example, the signal light emitted from one process chamber is attributed to a different process chamber, erroneous test results may result. The phenomenon of signal light emitted from a first process chamber and transmitted to a second process chamber is commonly referred to as "cross-talk." Cross-talk can lead to erroneous results when, for example, the second process chamber would not emit any signal light alone, but the signal light transmitted to the second process chamber from the first process chamber is detected and recorded as a false positive result.

Attempts to avoid cross-talk may include increasing the distance between the process chambers such that any signal light reaching the second process chamber is too weak to register as a positive result with a detector. Other approaches include masking or shrouding the process chambers using an external device located over the process chambers such as is described in International Publication No. WO 02/01180 A2 (Bedingham et al.). One problem with these approaches is that process chamber density on a device may be limited, resulting in a less than desired number of tests being performed on a given sample processing device. Another potential problem with these approaches is that they require the use of articles or materials (e.g., masks, shrouds, etc.) in addition to the sample processing devices, thus increasing the cost and complexity of using the sample processing devices.

Another situation in which the issue of isolation between process chambers from cross-talk may arise in the delivery of interrogating light to the process chambers. For example, it may be desired that not all of the process chambers be interrogated at the same time. In other words, the process chambers may be interrogated serially (i.e., one at a time) or only selected groups of process chambers may be interrogated at the same time. In such a situation, it may be preferred that none or limited amounts of the interrogating light be transmitted to the process chambers that are not the subject of interrogation. With known processing devices, the control over interrogating light may require the use of masks or shrouds, thus raising the same problems of limited process chamber density, as well as the cost and complexity added by the additional articles/process steps.

Other problems associated with processing devices include control over the feature size, shape, and location. For example, it may be desired that variations in process chamber sizes, shapes, locations, etc., as well as the size, shape and location of other features in the devices (e.g., delivery conduits, loading chambers, etc.) be limited. Variations in feature size may detrimentally affect test accuracy by, e.g., changing the volume of analyte in the different process chambers. Further, variations in feature size may require additional sample volume to, e.g., ensure filling of all process chambers, etc. Variations in feature shape may, e.g., affect the signal light density emitted from a process chamber. Variations in feature location may, e.g., reduce test accuracy if process chamber location is not repeatable between different processing devices.

SUMMARY

The present invention provides sample processing devices that include transmissive layers and control layers to reduce or eliminate cross-talk between process chambers in the processing device. The transmissive layers preferably transmit significant portions of signal light and/or interrogation light while the control layers block significant portions of signal light and/or interrogation light.

The present invention also provides methods of manufacturing processing devices that include transmissive layers and control layers. The methods may, in some embodiments, involve continuous forming processes including co-extrusion of materials to form the transmissive layer and control layer in a processing device, followed by formation of the process chambers in the control layer. In other embodiments, the methods may involve extrusion of materials for the control layer, followed by formation of process chambers in the control layer.

The control layers used in processing devices and methods of the present invention are provided to block the transmission of selected light where the "selected light" may be light of one or more particular wavelengths, one or more ranges of wavelengths, one or more polarization states, or combinations thereof. As used in connection with the present invention, "blocking" of light involves one or more of absorption, reflection, refraction, or diffusion of the selected light. In the case of signal light, transmission of the signal light through the control layer is preferably prevented or reduced to levels that will not result in false positive readings from process chambers. In the case of interrogation light, transmission of the interrogation light through the control layer is preferably prevented or reduced to levels that will not result in unwanted interrogation of process chambers. The control layers may block light of selected wavelengths or ranges of wavelengths. The control layers may also block light of one or more selected polarization states (e.g., s polarization, p polarization, circular polarization, etc).

As used in connection with the present invention, the term "light" will be used to refer to electromagnetic energy, whether visible to the human eye or not. It may be preferred that the light fall within a range of ultraviolet to infrared electromagnetic energy, and, in some instances, it may be preferred that light include electromagnetic energy in the spectrum visible to the human eye.

The processing devices of the present invention may provide a number of potential advantages. For example, by blocking the transmission of signal light, cross-talk during emission of signal light can be reduced or eliminated. With respect to the delivery of interrogation light, blocking the transmission of interrogation light to selected process chambers can reduce or eliminate unwanted interrogation of the selected process chambers.

Furthermore, the methods of the present invention may provide for fast and economical manufacturing of processing devices including both transmissive layers and control layers. Further, the methods may provide processing devices including features (e.g., process chambers, distribution conduits, etc.) that are accurately sized shaped and located.

In one aspect, the present invention provides a sample processing device including a body with a transmissive layer that transmits selected light and a control layer that blocks the selected light, wherein the control layer is attached to the transmissive layer with a first major surface of the control layer facing the transmissive layer and a second major surface facing away from the transmissive layer; a plurality of process chamber structures formed in the control layer, wherein each of the process chamber structures includes an interior window surface and an interior side surface formed by the control layer; a cover sheet attached to the second major surface of the control layer, wherein the cover sheet and the plurality of process chamber structures define a plurality of process chambers in the sample processing device, wherein the selected light can be transmitted into or out of each process chamber through the interior window surface; and a conduit in the sample processing device, wherein each process chamber of the plurality of process chambers is in fluid communication with the conduit.

In another aspect, the present invention provides a sample processing device including a body with a transmissive layer that transmits selected light and a control layer that blocks the selected light, wherein a first major surface of the control layer faces and is melt-bonded to the transmissive layer, and wherein a second major surface of the control layer faces away from the transmissive layer; a plurality of process chamber structures formed in the body, wherein each of the process chamber structures includes a void formed through the first major surface and the second major surface of the control layer, wherein the void exposes an interior window surface formed by the transmissive layer within each process chamber structure; a cover sheet attached to the second major surface of the control layer, wherein the cover sheet and the plurality of process chamber structures define a plurality of process chambers in the sample processing device, and wherein the cover sheet blocks the selected light; and a conduit formed between the cover sheet and the control layer in the sample processing device, wherein each process chamber of the plurality of process chambers is in fluid communication with the conduit.

In another aspect, the present invention provides a method of manufacturing a sample processing device, the method including providing a body that includes a transmissive layer that transmits selected light; a control layer that blocks the selected light, wherein the control layer is attached to the transmissive layer with a first major surface of the control layer facing the transmissive layer and a second major surface facing away from the transmissive layer; a plurality of process chamber structures formed in the control layer, wherein each of the process chamber structures includes an interior window surface and an interior side surface formed by the control layer; and attaching a cover sheet to the second major surface of the control layer, wherein the cover sheet and the plurality of process chamber structures define a plurality of process chambers in the sample processing device, and wherein attaching the cover sheet forms a conduit in the sample processing device, wherein each process chamber of the plurality of process chambers is in fluid communication with the conduit.

In another aspect, the present invention provides a sample processing device including a body with a first major surface and a second major surface, wherein the second major surface is flat, and wherein the body blocks selected light; a plurality of process chamber structures formed in the body, wherein the process chamber structures are formed into the first major surface of the body; a cover sheet attached to the first major surface of the body, wherein the cover sheet and the plurality of process chamber structures define a plurality of process chambers in the sample processing device, and wherein the cover sheet transmits the selected light; and a conduit located between the body and the cover sheet, wherein each process chamber of the plurality of process chambers is in fluid communication with the conduit.

In another aspect, the present invention provides a method of manufacturing a sample processing device, the method including providing a body that includes a first major surface and a second major surface, wherein the second major surface is flat, and wherein the body blocks selected light, wherein the body further includes a plurality of process chamber structures formed in the first major surface of the body; and attaching a cover sheet to the first major surface of the body, wherein the cover sheet and the plurality of process chamber structures define a plurality of process chambers in the sample processing device; and wherein attaching the cover sheet forms a conduit in the sample processing device, wherein each process chamber of the plurality of process chambers is in fluid communication with the conduit.

These and other features and advantages may be described below in connection with various illustrative embodiments of the invention.

DETAILED DESCRIPTION OF ILLUSTRATIVE EMBODIMENTS OF THE INVENTION

In the following detailed description of illustrative embodiments, reference is made to the accompanying figures of the drawing which form a part hereof, and in which are shown, by way of illustration, specific embodiments in which the invention may be practiced. It is to be understood that other embodiments may be utilized and structural changes may be made without departing from the scope of the present invention.

The present invention provides a sample processing device that can be used in the processing of liquid sample materials (or sample materials entrained in a liquid) in multiple process chambers to obtain desired reactions, e.g., PCR amplification, ligase chain reaction (LCR), self-sustaining sequence replication, enzyme kinetic studies, homogeneous ligand binding assays, and other chemical, biochemical, or other reactions that may, e.g., require precise and/or rapid thermal variations. More particularly, the present invention provides sample processing devices that include one or more process arrays, each of which include a loading chamber, a plurality of process chambers and a main conduit placing the process chambers in fluid communication with the loading chamber.

Although various constructions of illustrative embodiments are described below, sample processing devices of the present invention may be similar to those described in, e.g., International Publication Nos. WO 02/01180 and WO 02/00347 (both to Bedingham et al.). The documents identified above all disclose a variety of different features that could be incorporated into sample processing devices of the present invention.

Figure 1:
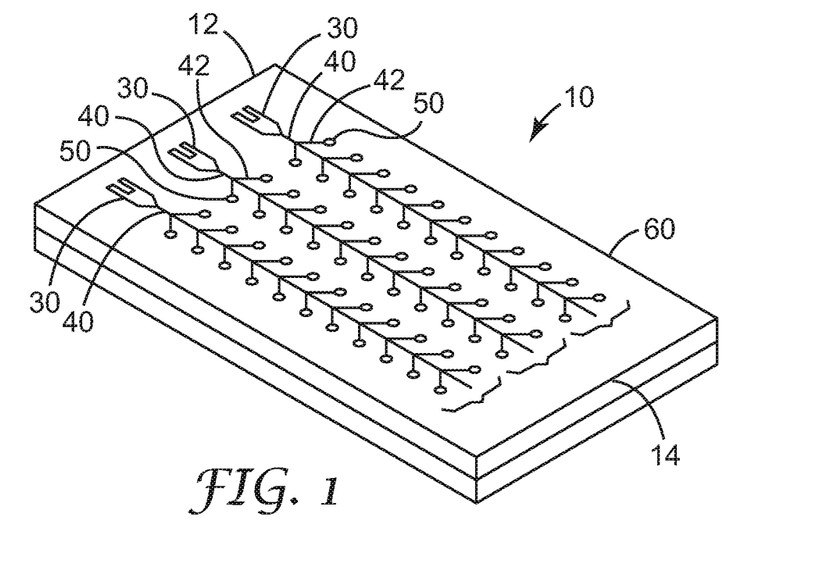
FIG. 1 is a perspective view of one illustrative processing device according to the present invention with the cover removed to expose the structures formed therein.
Figure 2:
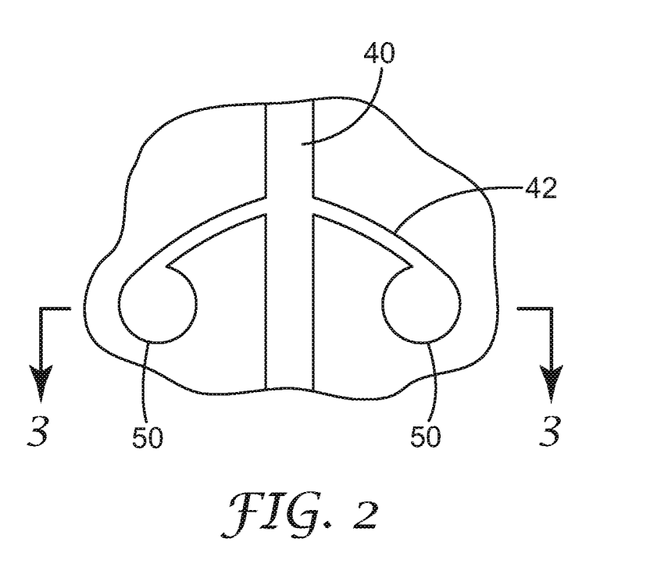
FIG. 2 is an enlarged view of a portion of the processing device of FIG. 1.

One illustrative sample processing device manufactured according to the principles of the present invention is illustrated in FIGS. 1 & 2, where FIG. 1 is a perspective view of one sample processing device 10 and FIG. 2 is an enlarged plan view of a portion of the sample processing device 10. In both views, a cover (described below in connection with FIG. 3) has been removed to expose structures formed in the body 60 of the device 10.

The sample processing device 10 includes at least one, and preferably a plurality of process arrays 20. Each of the depicted process arrays 20 preferably extends from proximate a first end 12 towards the second end 14 of the sample processing device 10. The process arrays 20 are depicted as being substantially parallel in their arrangement on the sample processing device 10. Although this arrangement may be preferred, it will be understood that any arrangement of process arrays 20 may alternatively be preferred.

Alignment of the process arrays 20 as depicted may be useful if the main conduits 40 of the process arrays are to be closed simultaneously as discussed in, e.g., International Publication No. WO 02/01180. Alignment of the process arrays 20 may also be useful if sample materials are to be distributed throughout the sample processing device by rotation about an axis of rotation proximate the first end 12 of the device 10 as discussed in, e.g., International Publication No. WO 02/01180.

Each of the process arrays 20 in the depicted embodiment includes at least one main conduit 40, and a plurality of process chambers 50 located along each main conduit 40. The process arrays 20 may also preferably include a loading structure in fluid communication with a main conduit 40 to facilitate delivery of sample material to the process chambers 50 through the main conduit 40. It may be preferred that, as depicted in FIG. 1, each of the process arrays include only one loading structure 30 and only one main conduit 40.

The loading structure 30 may be designed to mate with an external apparatus (e.g., a pipette, hollow syringe, or other fluid delivery apparatus) to receive the sample material. The loading structure 30 itself may define a volume or it may define no specific volume, but, instead, be a location at which sample material is to be introduced. For example, the loading structure may be provided in the form of a port through which a pipette or needle is to be inserted. In one embodiment, the loading structure may be, e.g., a designated location along the main conduit that is adapted to receive a pipette, syringe needle, etc. The loading may be performed manually or by an automated system (e.g., robotic, etc.). Further, the processing device 10 may be loaded directly from another device (using an automated system or manually).

The loading chamber depicted in FIG. 1 is only one embodiment of a loading structure 30 in fluid communication with the main conduit 40. It may be preferred that the loading chamber volume, i.e., the volume defined by the loading chamber (if so provided), be equal to or greater than the combined volume of the main conduit 40, process chambers 50, and feeder conduits 42 (if any).

The process chambers 50 are in fluid communication with the main conduit 40 through feeder conduits 42. As a result, the loading structure 30 in each of the process arrays 20 is in fluid communication with each of the process chambers 50 located along the main conduit 40 leading to the loading structure 30. If desired, each of the process arrays 20 may also include an optional drain chamber (not shown) located at the end of the main conduit 40 opposite the loading structure 30.

Figure 3:
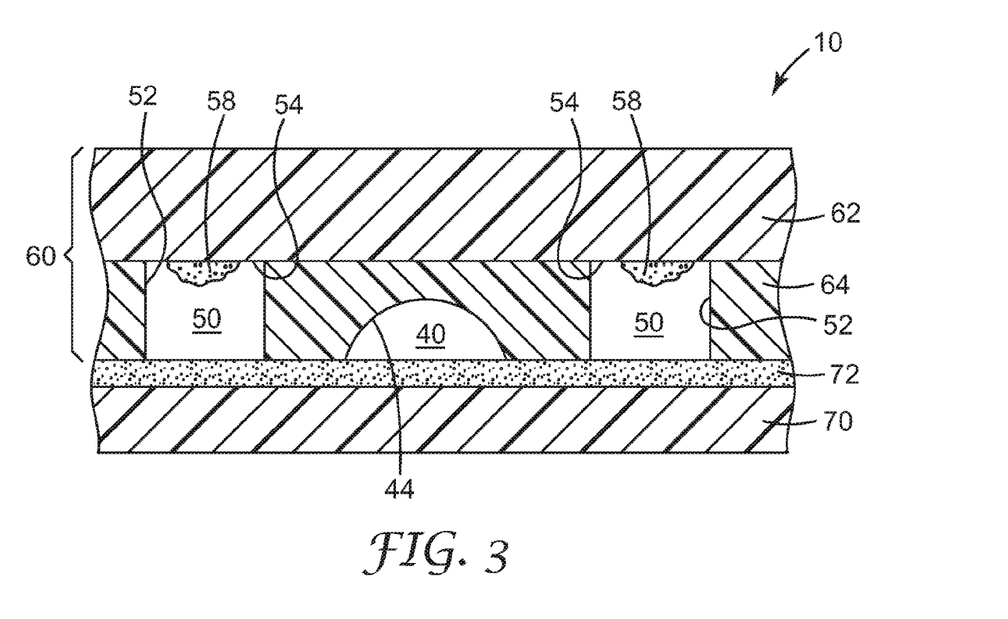
FIG. 3 is a cross-sectional view of FIG. 2 taken along line 3-3 in FIG. 2, with the cover located thereon.

FIG. 3 is a cross-sectional view of the portion of the processing device 10 depicted in FIG. 2 taken along line 3-3 in FIG. 2. The processing device 10 includes a body 60 that includes a transmissive layer 62 and control layer 64. It may be preferred that the transmissive layer 62 and control layer 64 be attached by a melt bond. As used herein, a "melt bond" is a bond formed by the melting and/or mixing of materials such as that occurring during, e.g., heat sealing, thermal welding, ultrasonic welding, chemical welding, solvent bonding, coextrusion, extrusion casting, etc. In such a bond, the materials facing each other in transmissive layer 62 and control layer 64 must be compatible with melt bonding so that an attachment of sufficient integrity can be formed to withstand the forces experienced during processing of sample materials in the process chambers.

Alternatively, the transmissive layer 62 and control layer 64 may be attached to each other using, e.g., adhesives, combinations of melt bonding and adhesives, etc. Examples of some attachment techniques may be described in, e.g., International Publication No. WO 02/01180.

The transmissive layer 62 is preferably constructed of one or more materials such that the transmissive layer 62 transmits significant portions of selected light. For the purposes of the present invention, significant portions may be, e.g., 50% or more of normal incident selected light, more preferably 75% or more of normal incident selected light. As discussed above, the selected light may be light of one or more particular wavelengths, one or more ranges of wavelengths, one or more polarization states, or combinations thereof. Examples of some suitable materials for the transmissive layer 62 include, but are not limited to, e.g., polypropylenes, polyesters, polycarbonates, polyethylenes, polypropylene-polyethylene copolymers, cyclo-olefin polymers (e.g., polydicyclopentadiene), etc.

The control layer 64 is preferably constructed of one or more materials such that the control layer 64 blocks significant portions of selected light. For the purposes of the present invention, significant portions of blocked light may be, e.g., 50% or more of normal incident selected light, more preferably 75% or more of normal incident selected light, and even more preferably 90% or more of normal incident selected light. As discussed above, the selected light may be one or more particular wavelengths, one or more ranges of wavelengths, one or more polarization states, or combinations thereof. Examples of some suitable materials for the control layer 64 include, but are not limited to, e.g., polypropylenes, polyesters, polycarbonates, polyethylenes, polypropylene-polyethylene copolymers, cyclo-olefin polymers (e.g., polydicyclopentadiene), etc., that have been modified to provide the desired light blocking function. For example, the material used for the control layer 64 may include a light blocking filler (e.g., colorants, carbon black, metallic particles, etc.) to prevent or reduce transmission of selected light through the control layer 64. In other instances, the control layer 64 may include a coating or other treatment that provides the desired light blocking function.

Where a melt bond between transmissive layer 62 and control layer 64 is to be formed, it may be preferred that the transmissive layer 62 and the control layer 64 be formed of compatible materials, in some instances, it may be preferred that the transmissive layer 62 and the control layer 64 be formed of the same polymeric material.

The processing device 10 includes process chambers 50 and a main conduit 40 located between the body 60 and the cover sheet 70. Cover sheet 70 is attached to the surface 65 of the control layer 64 facing away from the transmissive layer 62 using adhesive 72. The cover sheet 70 may, however, be attached to the control layer 64 by any suitable technique or combination of techniques, e.g., adhesives, combinations of melt bonding and adhesives, etc. Examples of some suitable attachment techniques may be described in, e.g., International Publication No. WO 02/01180.

The process chambers 50 are, in the depicted embodiment, defined by process chamber structures formed in the control layer 64 of the body 60 and the cover sheet 70 attached to the control layer 64. In the depicted embodiment, the process chamber structures are in the form of voids formed through the control layer 64, the voids including interior side surfaces 52. An interior window surface 54 is also formed within the process chamber 50 by a portion of the transmissive layer 62 exposed by the void in the control layer 64. As such, the process chambers 50 may be described as having a height measured from the cover sheet 70 to the interior window surface 54. Furthermore, it may be preferred that the control layer 64 have a thickness between the cover sheet 70 and the transmissive layer 62 that is less than or equal to the height of each process chamber 50. If the height of the process chamber 50 is greater than the thickness of the control layer 64, the transmissive layer 62 may preferably be thinned or otherwise deformed in the area of the window surface 54.

Although the depicted process chamber structure is formed as a void that exposes a portion of the transmissive layer 62 within the interior window surface 54, it should be understood that, in some instances, it may be acceptable if a relatively thin portion of the control layer 64 remains in the area occupied by the window surface 54. Any such relatively thin portion of the control layer 64 should, however, be sufficiently thin such that transmission of the selected light through the window surface 54 is still possible.

The process chamber structure also preferably includes one or more interior side surfaces 52 as depicted that are formed by the control layer 64. The interior side surfaces 52 may take any suitable shape, although it may be preferred that they extend from one major surface of the control layer 64 to the opposite major surface of the control layer 64.

FIG. 3 also depicts that the process chambers 50 may include a reagent 58 located therein. It may be preferred that at least some, and preferably all, of the process chambers 50 in the devices 10 of the present invention contain at least one reagent before the cover sheet 70 is attached to the body 60. The reagent 58 may be fixed within the process chamber 50 as depicted in FIG. 3 or it may be loose within the process chamber 50. The reagent 58 is optional, i.e., sample processing devices 10 of the present invention may or may not include any reagents 58 in the process chambers 50. In another variation, some of the process chambers 50 may include a reagent 58, while others do not. In yet another variation, different process chambers 50 may contain different reagents (in which case it may be desirable to fix the reagents to a surface within each process chamber 50).

Further, the interior of the process chamber structures may be coated or otherwise processed to control the adhesion of reagents 58. Also, in some instances, reagents may be provided on the cover sheet 70.

Although the cover sheet 70 is depicted as generally flat, it should be understood that the cover sheet 70 may deviate from a flat sheet if so desired. For example, the cover sheet 70 may be formed to increase or decrease the volume of the process chamber 50.

The cover sheet 70 may be provided as, e.g., a sheet of metal foil, polymeric material, multi-layer composite, etc. that is attached to the control layer 64 over the process chamber structures 52 to form process chambers 50. Although the cover sheet 70 is depicted as a unitary homogenous layer, it should be understood that the cover sheet 70 may include one or materials and those materials may be provided in different layers or they may be intermixed within the cover sheet 70.

If the cover sheet 70 includes a metallic foil, the cover sheet 70 may preferably include a passivation layer on the surfaces that face the interiors of the process chambers 50 and main conduit 40 to prevent contamination of the sample materials by the metal. As an alternative to a separate passivation layer, any adhesive layer 72 used to attached the cover sheet 70 to the control layer 64 may also serve as a passivation layer to prevent contact between the sample materials and any metallic layer in the cover sheet 70. The cover sheet 70 may preferably be deformable such that the main conduits 40 can be closed or sealed as described in, e.g., International Publication No. WO 02/01180.

In some embodiments, it may be preferred that the cover sheet 70 and adhesive 72 (if present) provide a reflective surface facing the interior of the process chambers 50 for the selected light. The reflectivity may be provided by, e.g., a metallic surface of the cover sheet 70, by the adhesive 72 itself, or by a reflective polymeric sheet used to form the cover sheet 70, or any other reflective structure or material.

In other embodiments, it may be preferred that the cover sheet 70 be transmissive such that it transmits the selected light. In such an embodiment, the process chambers 50 may be interrogated by light that may be absorbed by one or more components within the process chamber 50. If both the transmissive layer 62 and the cover 70 are transmissive to the selected light, a detector could be positioned on the side of the processing device opposite from the side at which the selected light is directed into the process chamber 50. For example, if the selected light is directed into the process chamber 50 through the transmissive layer 62, the detector may be placed on the same side as the cover 70 such that the selected light is either absorbed within the process chamber 50 or transmitted through the transmissive layer 62, process chamber 50 and cover 70 before reaching the detector. Such absorption may be used to determine the presence or absence of one or more analytes within the process chamber 50. Alternatively, signal light from, e.g., chemiluminescence in the process chamber 50 may be transmitted out of the process chamber 50 through either the transmissive layer 62 or the transmissive cover 70.

A variety of adhesives 72 may be used, although any adhesive selected should be capable of withstanding the forces generated during processing of any sample materials located in the process chambers 50, e.g., forces developed during distribution of the sample materials, forces developed during thermal processing of the sample materials, etc. Those forces may be large where, e.g., the processing involves thermal cycling as in, e.g., polymerase chain reaction and similar processes. It may also be preferred that any adhesives used in connection with the sample processing devices exhibit low fluorescence, be compatible with the processes and materials to be used in connection with sample processing devices, e.g. PCR, etc.

It may be preferred to use adhesives that exhibit pressure sensitive properties. Such adhesives may be more amenable to high volume production of sample processing devices since they typically do not involve the high temperature bonding processes used in melt bonding, nor do they present the handling problems inherent in use of liquid adhesives, solvent bonding, ultrasonic bonding, and the like. Techniques for identifying and selecting pressure sensitive adhesives are discussed in, e.g., International Publication No. WO 02/01180.

It may be preferred that the pressure sensitive adhesives used in connection with the sample processing devices of the present invention include materials which ensure that the properties of the adhesive are not adversely affected by water. For example, the pressure sensitive adhesive will preferably not lose adhesion, lose cohesive strength, soften, swell, or opacify in response to exposure to water during sample loading and processing. Also, the pressure sensitive adhesive should not contain any components which may be extracted into water during sample processing, thus possibly compromising the device performance.

In view of these considerations, it may be preferred that the pressure sensitive adhesive be composed of hydrophobic materials. As such, it may be preferred that the pressure sensitive adhesive be composed of silicone materials. Some suitable compositions may be described in International Publication WO 00/68336 titled SILICONE ADHESIVES, ARTICLES, AND METHODS (Ko et al.).

Also depicted in the embodiment of FIG. 3 is a cross-sectional view of the main conduit 40 that is in fluid communication with the process chambers 50. The main conduit 40, in the depicted embodiment, is defined by conduit structure 44 formed in the control layer 64 of the body 60 and the cover sheet 70 attached to the control layer 64. In the depicted embodiment, the conduit structure 44 is in the form of a channel formed into the surface of the control layer 64 facing away from the transmissive layer 62. As such, the conduit structure 44 may be described as having a height measured from the cover sheet 70 towards the transmissive layer 62. Furthermore, it may be preferred that the height of the conduit structure 44 be less than the thickness of the control layer 64 (as measured between the opposing major surfaces of the control layer 64) such that, e.g., none of the transmissive layer 62 be exposed within the conduit structure 44.

Although the cover sheet 70 is depicted as generally flat, it should be understood that the cover sheet 70 may deviate from a flat sheet if so desired. For example, the cover sheet 70 may be formed to increase or decrease the cross-sectional area of the conduit 40 (in the view as seen in FIG. 3).

Further, it may be preferred that the shape of the conduit structure 44 and the materials selected for the control layer 64, the cover sheet 70 and the adhesive 72 be such that the conduit 40 can be sealed or occluded by deforming the cover sheet 70 into the conduit structure 44 as described in, e.g., International Publication No. WO 02/01180.

Figure 4:
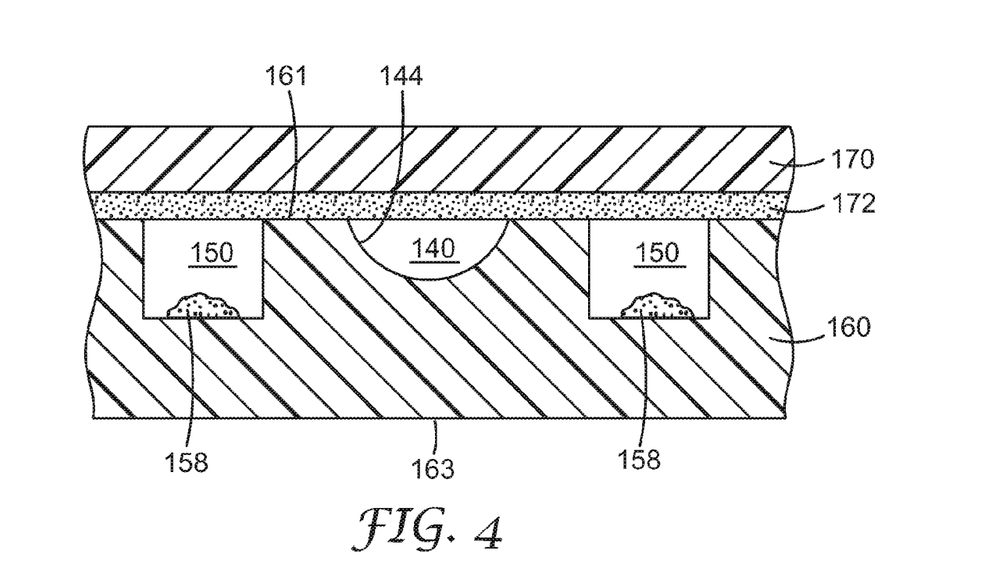
FIG. 4 is a cross-sectional view of an alternative processing device according to the present invention.

FIG. 4 depicts an alternative construction for a sample processing device according to the present invention. The processing device is formed by a body 160 and a cover sheet 170. In this embodiment, however, the body 160 is preferably formed of a material or materials that block the transmission of selected light between the process chambers 150.

Transmission of the selected light into and/or out of the process chambers 150 occurs, instead, through the cover sheet 170 which preferably transmits significant portions of the selected light. For the purposes of the present invention, significant portions may be, e.g., 50% or more of normal incident selected light, more preferably 75% or more of normal incident selected light. As discussed above, the selected light may be one or more particular wavelengths, one or more ranges of wavelengths, one or more polarization states, or combinations thereof. Examples of some suitable materials for the cover sheet 170 include, but are not limited to, e.g., polypropylenes, polyesters, polycarbonates, polyethylenes, polypropylene-polyethylene copolymers, cyclo-olefin polymers (e.g., polydicyclopentadiene), etc.

Although the cover sheet 170 is depicted as a unitary homogenous layer, it should be understood that the cover sheet 170 may include one or materials and those materials may be provided in different layers or they may be intermixed within the cover sheet 170.

The body 160 is preferably constructed of one or more materials such that the body 160 blocks transmission of significant portions of selected light. For the purposes of the present invention, significant portions of blocked light may be, e.g., 50% or more of normal incident selected light, more preferably 75% or more of normal incident select light, and even more preferably 90% or more of normal incident selected light. As discussed above, the selected light may be one or more particular wavelengths, one or more ranges of wavelengths, one or more polarization states, or combinations thereof.

Examples of some suitable materials for the body 160 include, but are not limited to, e.g., polypropylenes, polyesters, polycarbonates, polyethylenes, polypropylene-polyethylene copolymers, cyclo-olefin polymers (e.g., polydicyclopentadiene), etc., that have been modified to provide the desired light blocking function. For example, the material used for the body 160 may include a light blocking filler (e.g., colorants, carbon black, metallic particles, etc.) to prevent or reduce transmission of selected light through the body 160. In other instances, the body 160 may include a coating or other treatment that provides the desired light blocking function.

The processing device includes process chambers 150 and a main conduit 140 located between the body 160 and the cover sheet 170. The process chambers 150 are, in the depicted embodiment, defined by process chamber structures 152 formed in the surface 161 of body 160 and the cover sheet 170 attached to the body 160. In the depicted embodiment, the process chamber structures 152 are in the form of depressions formed into the body, but not through the entire thickness of the body 160. Although the cover sheet 170 is depicted as generally flat, it should be understood that the cover sheet 170 may deviate from a flat sheet if so desired. For example, the cover sheet 170 may be formed to increase or decrease the volume of the process chamber 150.

Cover sheet 170 is attached to the surface 161 of the body 160 using adhesive 172. The cover sheet 170 may, however, be attached to the body 160 by any suitable technique or combination of techniques, e.g., adhesives, combinations of melt bonding and adhesives, etc. Examples of some suitable attachment techniques may be described above with respect to adhesive 72 on cover sheet 70 in FIG. 3, as well as in, e.g., International Publication No. WO 02/01180.

Also depicted in the embodiment of FIG. 4 is a cross-sectional view of the main conduit 140 that is in fluid communication with the process chambers 150. The main conduit 140, in the depicted embodiment, is defined by conduit structure 144 formed in the body 160 and the cover sheet 170 attached to the body 160. In the depicted embodiment, the conduit structure 144 is in the form of a channel formed into the surface 161 facing the cover sheet 170. As such, the conduit structure 144 may be described as having a height measured from the cover sheet 170 towards the opposing surface 163 of the body 160. Furthermore, it may be preferred that the height of the conduit structure 144 be less than the thickness of the body 160 as measured between opposite major surfaces 161 and 163.

Figure 5:
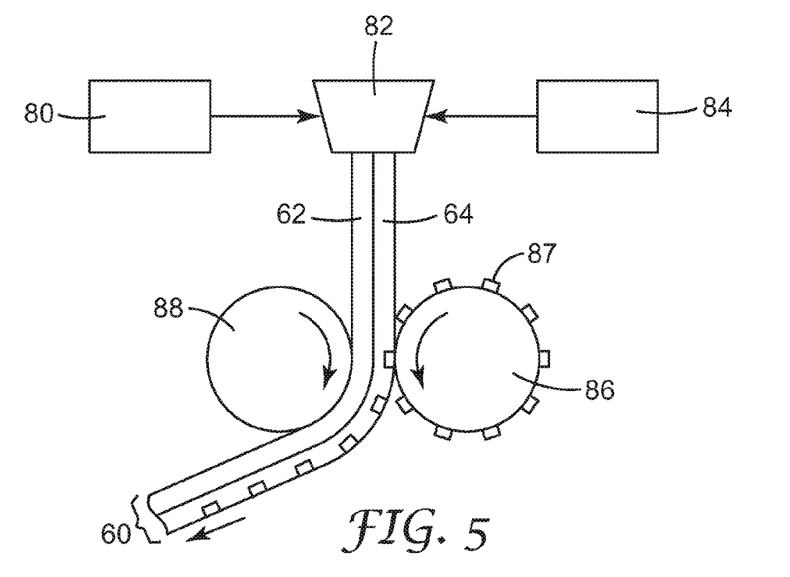
FIG. 5 is a schematic diagram of a portion of one manufacturing process according to the present invention.

The processing devices of the present invention may be manufactured by a variety of methods and techniques. A portion of one exemplary manufacturing method is depicted in FIG. 5 for manufacturing processing devices including a body having a transmissive layer and control layer as described in connection with FIG. 3. A melt-processable polymer for the transmissive layer 62 is delivered from an extruder 80 to multi-layer feedblock and film die 82. At the same time, a melt-processable polymer for the control layer 64 is delivered from extruder 84 the multi-layer feedblock and film die 82. The two melt-processable polymers streams are delivered to the multi-layer feedblock and film die 82 at or above their melt-processing temperature. The multi-layer feedblock and film die 82 preferably keeps the two polymer melt streams from extruders 80 and 84 separated such that the two polymers form separate and discrete layers 62 and 64.

The layers 62 and 64 of polymer are discharged from the multi-layer feedblock and film die 82 onto a forming tool 86. It may be preferred that the polymers be drop cast onto the surface of the forming tool 86 at a point near the nip between forming tool 86 and backup roll 88.

The forming tool 86 includes protrusions 87 extending therefrom that correspond to the various features to be formed in the processing devices, e.g., process chambers, conduits, etc. It may be preferred that the thickness of each of layers 62 and 64 be controlled such that the thickness of layer 64 is less than or equal to the height of the protrusions 87 that form the process chamber structures in the processing devices of the present invention. Limiting the thickness of layer 64 in that manner can provide for process chamber structures in layer 64 that are formed as voids as described above with respect to FIG. 3.

It may be preferred that at least the control layer 64 be delivered to the forming tool 86 at a temperature that is at or above its melt processing temperature (i.e., the temperature at which it can be formed or molded). By providing the control layer 64 to the forming tool 86 at or above its melt processing temperature, the polymer in the control layer can adequately form or be replicated to the shape of the protrusions 87 on the forming tool 86. Although the forming tool 86 is depicted as a roll, it should be understood that it may alternatively be provided as a continuous belt or other structure amenable to continuous web-form processing.

It may also be preferred that the polymer of the transmissive layer 62 also be delivered to the nip formed by forming tool 86 and backup roll 88 at a temperature that is at or above its melt processing temperature such that the two layers 62 and 64 can be formed together to provide a melt bond between the two layers while the features of forming tool 86 are being formed into the control layer 64.

The temperatures of both layers 62 and 64 are preferably lowered to below their respective melt processing temperatures at some point after the nip with backup roll 88 to retain the structures formed in layer 64 and provide mechanical stability to the web.

The result of the processing depicted in FIG. 5 is a web including both a transmissive layer 62 and control layer 64 to form the body 60 of a processing device according to the present invention. The control layer 64 includes structures formed therein for, e.g., process chambers, conduits, loading chambers, etc.

Figure 6:
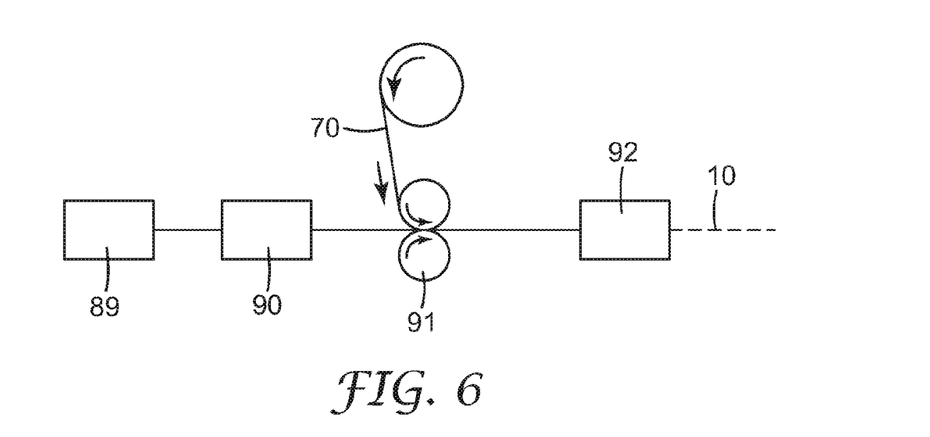
FIG. 6 is a schematic diagram of a system for manufacturing processing devices according to the present invention.

FIG. 6 is a schematic diagram of the larger process for manufacturing processing devices according to the present invention. The system depicted in FIG. 6 includes the components and process of FIG. 5 as apparatus 89. The web formed by apparatus 89 (including the transmissive layer and the control layer 64) may preferably be fed into a reagent station 90 where reagents can be added to, e.g., the process chamber structures as discussed herein. Following the addition of reagents, the web may preferably be fed into a laminating station 91 where a cover sheet web 70 is laminated thereto to form a composite web structure including process chambers 50, conduits 40, etc. The composite web may then preferably be delivered to a sheeting station 92 where the web is separated by, e.g., die cutting, into individual processing devices 10.

Figure 7:
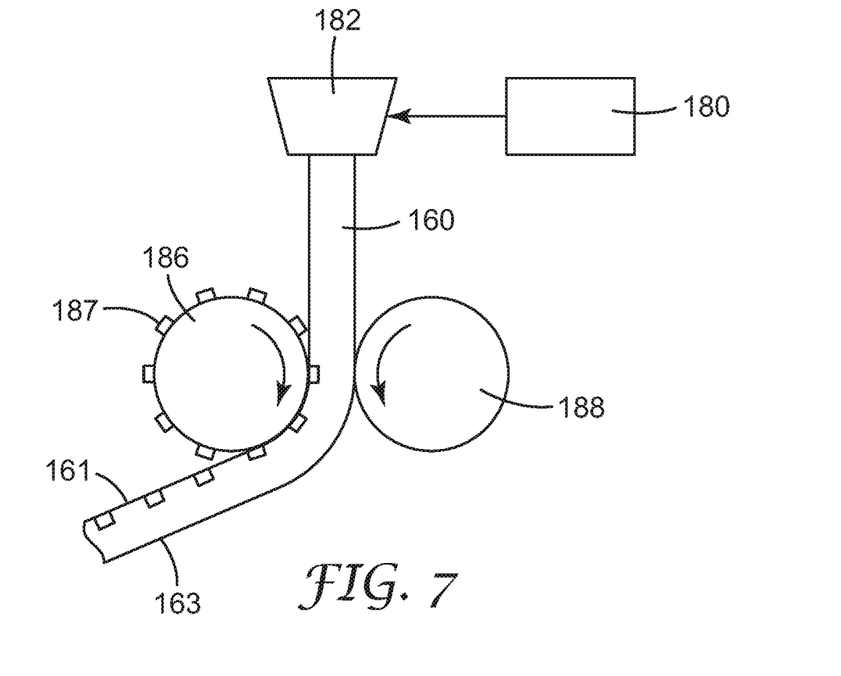
FIG. 7 is a schematic diagram of a portion of another manufacturing process according to the present invention.
Figure 8:
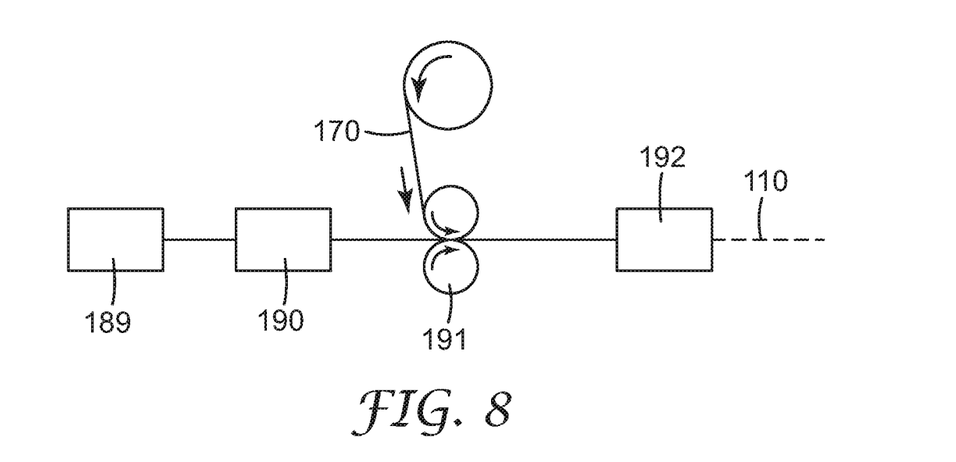
FIG. 8 is a schematic diagram of a system for manufacturing processing devices according to the present invention.

FIGS. 7 & 8 depict an alternative manufacturing process that may be used to, e.g., manufacture processing devices constructed as described in FIG. 4. The A melt-processable polymer for the body 160 is delivered from an extruder 180 to die 182. The melt-processable polymer stream is delivered to the die 182 at or above its melt-processing temperature.

The polymer layer 160 is discharged from the die 182 onto a forming tool 186. It may be preferred that the layer 160 be drop cast onto the forming tool 186 just before the nip formed with backup roll 188. The forming tool 186 includes protrusions 187 extending therefrom that correspond to the various features to be formed in the processing devices, e.g., process chambers, conduits, etc. It is preferred that the thickness of the polymer layer 160 be controlled such that the thickness of layer 160 is greater than the height of the protrusions 187 that form the process chamber structures in the processing devices of the present invention.

It may be preferred that the polymer layer 160 be delivered to the forming tool 186 at a temperature that is at or above its melt processing temperature (i.e., the temperature at which it can be formed or molded). By providing the polymer layer 160 to the forming tool 186 at or above its melt processing temperature, the polymer can adequately form or be replicated to the shape of the protrusions 187 on the forming tool 186. Although the forming tool 186 is depicted as a roll, it should be understood that it may alternatively be provided as a continuous belt or other structure amenable to continuous web-form processing.

The temperature of the polymer layer 160 is preferably lowered to below the melt processing temperature at some point after the nip with backup roll 188 to retain the structures formed in layer 160 and provide mechanical stability to the web. The result of the processing depicted in FIG. 7 is a web 160 that can be used to form the bodies of processing devices according to the present invention. The web 160 includes structures formed therein for, e.g., process chambers, conduits, loading chambers, etc.

FIG. 8 is a schematic diagram of the larger process for manufacturing processing devices according to the present invention. The system depicted in FIG. 8 includes the components and process of FIG. 7 as apparatus 189. The web formed by apparatus 189 may preferably be fed into a reagent station 190 where reagents can be added to, e.g., the process chamber structures as discussed herein. Following the addition of reagents, the web may preferably be fed into a laminating station 191 where a cover sheet web 170 is laminated thereto to form a composite web structure including process chambers, conduits, etc. The composite web may then preferably be delivered to a sheeting station 192 where the web is separated by, e.g., die cutting, into individual processing devices 110.

In an alternative process, the web formed by apparatus 189 may be sheeted before any reagents are added to the sheeted web. It may also be preferred that in such a process, the cover sheet web 170 be sheeted before it is laminated to the sheets formed from the web of apparatus 189.

All references and publications cited herein are expressly incorporated herein by reference in their entirety into this disclosure. Illustrative embodiments of this invention are discussed and reference has been made to possible variations within the scope of this invention. These and other variations and modifications in the invention will be apparent to those skilled in the art without departing from the scope of the invention, and it should be understood that this invention is not limited to the illustrative embodiments set forth herein. Accordingly, the invention is to be limited only by the claims provided below and equivalents thereof.

The invention claimed is:

1. A method of manufacturing a sample processing device, the method comprising:
   providing a multi-layer polymer melt stream having two separate and discrete layers, the layers comprising:
      a transmissive layer that transmits selected light; and
      a control layer that blocks the selected lights;
      wherein the control layer comprises a polymeric material at or above a melt processing temperature of the polymeric material;
      wherein the control layer is attached to the transmissive layer with a first major surface of the transmissive layer facing the control layer and a second major surface facing away from the control layer; and
   while the control layer is held at or above the melt processing temperature, forming a plurality of process chamber structures in the control layer such that each of the process chamber structures comprises an interior window surface proximate the first major surface and an interior side surface formed by the control layer, wherein the interior window surface within each process chamber structure is formed by a thinned portion of the control layer, and wherein the thinned portion of the control layer is sufficiently thin so that the thinned portion of the control layer transmits the selected light.

2. A method according to claim 1, wherein forming the plurality of process chamber structures comprises:
   lowering the temperature of the control layer below the melt processing temperature after forming the plurality of process chamber structures.

3. The method of claim 1, wherein the transmissive layer transmits significant portions of the selected light, and wherein the control layer blocks significant portions of the selected light.

4. The method of claim 1, wherein providing the control layer on the transmissive layer comprises providing the transmissive layer at a temperature that is at or above its melt processing temperature such that a melt bond is formed between the control layer and the transmissive layer while the process chamber structures are being formed into the control layer.

5. The method of claim 1, wherein forming a plurality of process chamber structures in the control layer comprises contacting a forming tool with the control layer while the polymeric material of the control layer is at or above its melt processing temperature.

* * * * *

UNITED STATES PATENT AND TRADEMARK OFFICE
CERTIFICATE OF CORRECTION

| | | |
|---|---|---|
| PATENT NO. | : 8,865,091 B2 | Page 1 of 1 |
| APPLICATION NO. | : 12/749763 | |
| DATED | : October 21, 2014 | |
| INVENTOR(S) | : Joel R. Dufresne et al. | |

It is certified that error appears in the above-identified patent and that said Letters Patent is hereby corrected as shown below:

Title Page, page 2
Column 2,
Item (56), References Cited, under OTHER PUBLICATIONS, line 2, "*Sesitive*" should read --*Sensitive*--.

In the Claims,
Column 13,
Line 27, claim 1 "lights;" should read --light;--.

Signed and Sealed this
Sixteenth Day of August, 2016

Michelle K. Lee
*Director of the United States Patent and Trademark Office*